United States Patent [19] [11] 3,989,625
Mason [45] Nov. 2, 1976

[54] DETECTOR FOR AIR IN BLOOD DIALYSIS SYSTEMS
[75] Inventor: Barry D. Mason, Burbank, Calif.
[73] Assignee: Ma-De Inc., Burbank, Calif.
[22] Filed: Feb. 25, 1975
[21] Appl. No.: 552,984

[52] U.S. Cl. .......................... 210/94; 128/214 E; 210/96 M; 210/321 B
[51] Int. Cl.² ........................................ B01D 31/00
[58] Field of Search ............ 128/214 E; 210/321 K, 210/94, 96, 85; 340/239, 237; 250/573, 574, 575

[56] References Cited
UNITED STATES PATENTS
3,416,664  12/1968  Kumme et al. .................. 210/321 X
3,812,482  5/1974  Clark............................ 128/214 E X
3,884,228  5/1975  Hahn............................ 128/214 E X
3,890,968  6/1975  Pierce et al. .................... 128/214 E
3,898,637  8/1975  Wolstenholme............. 128/214 E X
3,900,396  8/1975  Lamadrid............................ 210/94

Primary Examiner—Frank A. Spear, Jr.
Attorney, Agent, or Firm—Donald D. Mon

[57] ABSTRACT

A sensor system for detecting the absence of substantially air-free blood in a blood chamber of an artificial kidney dialysis system. The system includes a first and a second radiation source and sensor means responsive to said radiation. The sensor means is aligned with and intersects the axis of the first source, and is not aligned with and does not intersect the axis of the second source. Perception of sufficient radiation from the first source indicates absence of blood in the chamber. Perception of sufficient radiation from the second source indicates foam in the blood chamber. The sensor system can control valve means, and preferably can selectively be by-passed, and automatically be adjusted for sensitivity.

20 Claims, 14 Drawing Figures

DETECTOR FOR AIR IN BLOOD DIALYSIS SYSTEMS

This invention relates to the detection of air in a blood chamber in an artificial kidney dialysis system.

In the practice of artificial kidney dialysis, blood is withdrawn from the patient, is mechanically transported through an artificial kidney to remove impurities, and is then returned to the venous system of the patient. It is absolutely essential that the blood which is returned to the patient be free from air, because air injected into the blood stream can be fatal to the patient.

Air can enter the dialysis system as a consequence of momentary lack of a supply of blood during the pumping process, or from an air leak into the system. It may be evidenced either as an absence of blood at some level in a blood chamber, or by the presence of foamy blood therein. The latter is the more common circumstance. To detect the absence of substantially air-free blood from a blood chamber, it is necessary for a reliable system to respond both to the presence of air in the blood chamber in the sense of a complete absence of blood, and also to the presence of foamy blood. Devices have been suggested to give an alarm under these circumstances, but in general they suffer from the disadvantages of complexity, physical bulk, and sensitivity to surrounding ambient conditions, such as visible light, especially fluorescent lights, which confuse the device and give false alarms. Furthermore, many systems are not suitably adjustable for sensitivity to their surroundings so that, while they are safe under a limited set of conditions, they may be unsafe when the device is used at another location or on a different person's blood.

It is an object of this invention to provide a rugged, simple, and small detector system which can include means automatically to adjust its sensitivity for each run, and which can readily detect the absence of blood or the presence of foam in a blood chamber, then to give an alarm and to terminate the operation of the device.

A sensor system according to this invention is used to combination with a blood chamber which includes a wall having a transparent portion. The sensor system itself includes a first and a second radiation source, each of which has a respective axis of illumination. Sensor means is responsive to the radiation from these sources, the sensor means being aligned with and intersecting the axis of the first source, and being unaligned with and not intersecting the axis of the second source. The radiation from the first source is substantially focused on the sensor means and is directly perceived by it. Radiation from the second source illuminates a substantial area lying transverse to its own axis and is indirectly perceived by reflection from blood in the blood chamber. The sources and sensor means lie outside of and face toward the transparent portion of the blood chamber.

According to a preferred but optional feature of the invention, the sensor means has an active condition and a passive condition, one of the conditions being assumed as the consequence of detection of radiation from one of the sources, and in which control means is responsive to the said one condition of the sensor means to terminate the flow of fluid through the blood chamber.

According to another preferred but optional feature of the invention, the sensor means has a sensitivity level, and adjustment means is provided automatically to adjust said sensitivity level at the start of each dialysis run.

According to still another preferred but optional feature of the invention, said radiation is infrared radiation.

The above and other features of this invention will be fully understood from the following detailed description and the accompanying drawings, in which:

FIG. 4 is a fragmentary cross-section showing another embodiment of the invention;

Figure 1:
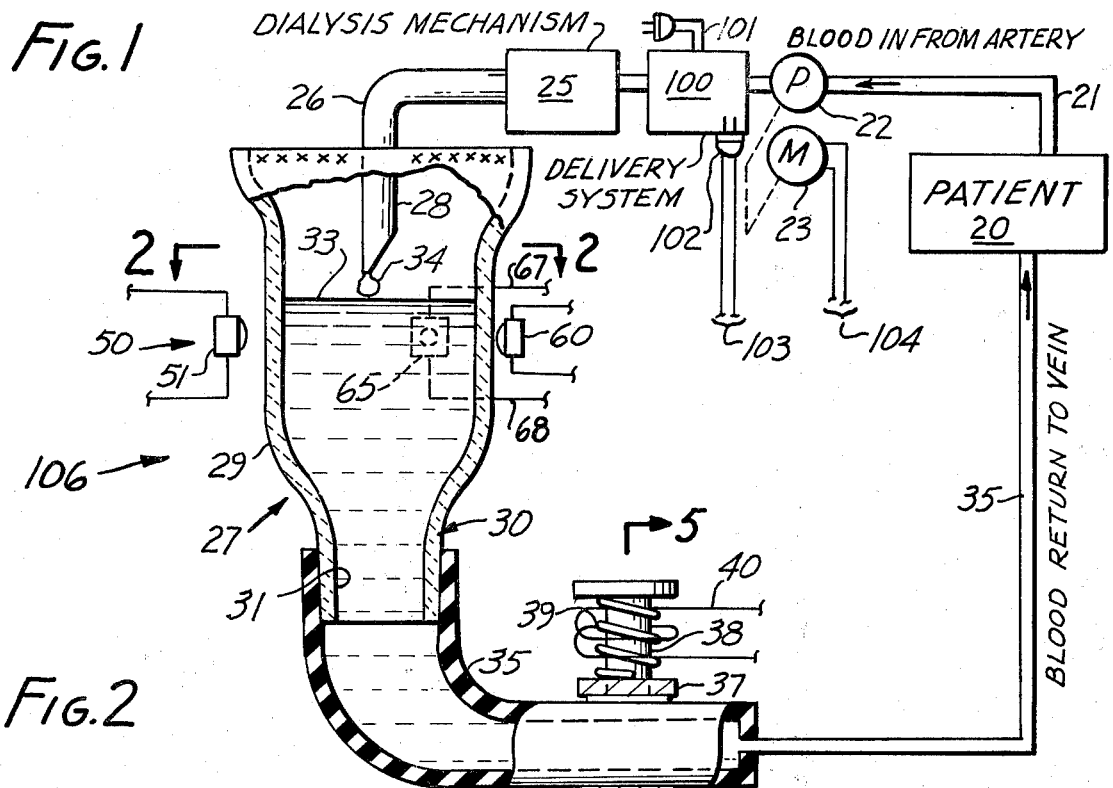
FIG. 1 is a side elevation, partly in schematic notation and partly in axial cross-section, showing the presently preferred embodiment of the invention.

The presently preferred embodiment of the invention is shown in FIG. 1. It is adapted and connected to provide dialysis treatment to a patient 20, from whose artery blood is withdrawn through an inlet conduit 21 by a mechanical pump 22 driven by an electrical motor 23. The pump forms part of a delivery system 100 which delivers the blood to a dialysis mechanism 25 of any suitable type wherein the blood is cleansed of its impurities by known techniques. The delivery system and the dialysis mechanism per se form no part of this invention, and will not be disclosed in detail here. However, the pump may be subject to control by the sensor system.

The cleansed blood is discharged from the dialysis mechanism through a discharge conduit 26 which enters a blood chamber 27 through a drip tube 28. The blood chamber has a wall 29, a portion of which, preferably all of which, is transparent. The blood chamber may conveniently include a lower portion 30 with a depending neck 31. Its wall forms the "transparent portion."

The purpose of the blood chamber is to permit visual observation of the blood flow so that it can be ascertained visually that blood is flowing and in proper condition. However, because dialysis takes so long a time, it is impractical for the device to be continuously monitored visually, and therefore automatic monitoring is a practical necessity. This invention provides a system for that purpose.

In FIG. 1 a blood level 33 (the top surface of a pool of blood in the blood chamber) is shown. Drops 34 of blood (or a stream depending on velocity) are shown leaving the drip tube to enter the pool of blood whose level is shown at 33. Because blood flow cannot be detected in a full blood chamber, it is customary to discharge it from a drip tube, as shown, leaving a region filled with air above level 33. Air bleed means (not shown) is often provided to admit air for this purpose. A return conduit 35 connects to the neck 31 of the blood chamber and returns to the patient's veins.

The entire blood chamber may be made of transparent glass or plastic. For convenience in use, it may be stiffly flexible. At least the portion of its wall immediately below level 33 will be transparent.

A valve 36 is provided in the return conduit, whose setting is selectible to permit or to prevent the flow of fluid from the blood chamber by closing or by leaving open the return conduit. The return conduit may conveniently be a flexible elastomeric conduit which can be pinched closed.

Figures 5, 6:
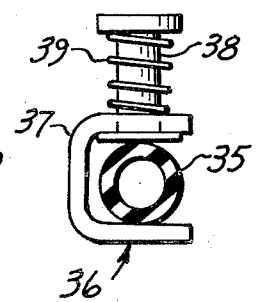
FIG. 5 is a cross-section taken at line 5—5 in FIG. 1.
FIG. 6 is a view similar to FIG. 5 in another operating condition.

For the above purpose, valve 36 may be provided as a clamp valve including a U-shaped anvil 37 which straddles the tube. The upper arm of the anvil slidably supports a plunger 38 which is spring-loaded by spring 39 to the open position. The valve includes a solenoid winding 40 which, when energized, causes the plunger (which is made of magnetizable material such as iron) to move down and against the return conduit to pinch it closed. FIGS. 5 and 6 show the open and closed positions, respectively. These positions are caused by the spring return of the plunger in the absence of energizing the winding, or by energizing the winding, respectively.

It is evident that other types of valving may be used instead, including solenoid-actuated mechanical valves placed directly in the stream. However, the illustrated clamp valve has the advantage of being disposed entirely outside of the blood stream, and it cannot introduce contaminants into the bloodstream. The valve is therefore preferably a solenoid-actuated valve which can close to prevent the flow of fluid when an alarm condition indicates that flow should be prevented.

Figure 2:
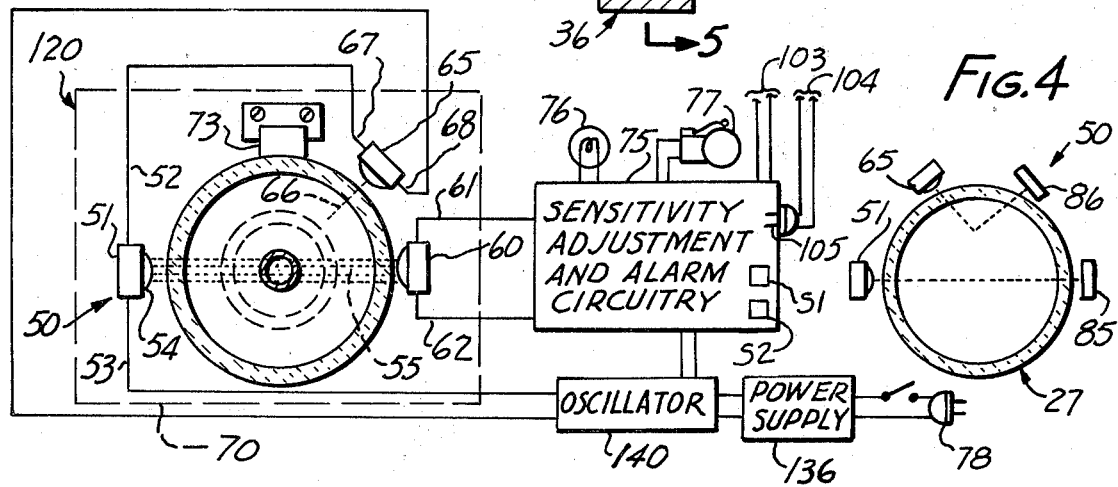
FIG. 2 is a cross-section taken at line 2—2 of FIG. 1.
Figure 3:
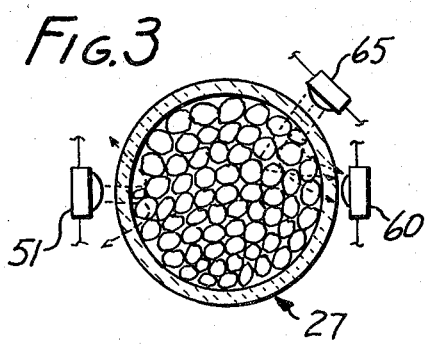
FIG. 3 is a fragmentary portion of FIG. 2 in another operating condition.

The sensor system 50 according to the invention is best shown in FIGS. 1 and 2. It includes a first radiation source 51 which is energized by current applied through leads 52, 53. This radiation source preferably has a focusing lens 54 with an axis of illumination 55. This radiation source is disposed outside the transparent portion of the blood chamber and is directed toward, and substantially focused upon, sensor means 60.

The sensor means is coaxial with axis 55 so it directly receives radiation from the first source. The sensor means has leads 61, 62 for inclusion within circuitry yet to be described.

A second radiation source 65 is, like the first radiation source and the sensor means, also disposed outside the blood chamber and faces the transparent portion thereof. The second radiation source is not well-focused. Instead of a focusing lens, it has a "flat" lens which provides a wider-spread illumination than the focused beam of the other radiation source. It may even be a somewhat diffuse or divergent source. A focusing lens could be used, but is less effective in providing radiation which is to be reflected.

Source 65 illuminates a substantial area which lies transverse to its axis of illumination 66. The sensor means is unaligned with axis 66 and does not intersect it. Instead, the angle between the axis of illumination of the second radiation source and the axis of the sensor means may be approximately 30° apart if they are at the same elevation on the blood chamber. Alternatively, the second source might be below the sensor means and directly upwardly at about the same angle relative to the sensor. Leads 67, 68 are provided to connect the second radiation source into a circuit.

The arrangement of the two radiation sources and the sensor means is such that radiation from the first source is directly focused on the sensor means and will be perceived by the sensor means unless material in the blood chamber obscures the same. The radiation from the second source 65 is not perceived directly. Instead, it is perceived (i.e., received or detected) by reflection from material in the blood chamber illuminated by the second radiation source. The theory of the second radiation source and the sensor means is that blood with air in it, for example foamy blood, will be more reflective than blood without air in it, and if there is air in the blood, more radiation will be reflected to the sensor, and this can be used as a means to sense the presence of foamy blood. Therefore, the sensor means is sensitive to the absence of material in the blood chamber if it receives radiation from the first source, and is sensitive to air in the blood if it receives radiation reflected by the blood from the second source in an amount representative of the presence of foam.

The radiation sources may use any desired form of radiation, for example infrared radiation, visible light, and weak laser coherent beams. However, it has been found most advantageous to utilize infrared radiation. This is for the reason that in the usual room where dialysis is done, there is little infrared radiation, for example from its lights. For example, there is substantially no infrared radiation from the fluorescent lights which are frequently used in these rooms. Accordingly, no false alarm will be caused by stray radiation, such as from variations in the illumination of the room or from X radiation or otherwise. It is a problem in some known devices that alarms can be set off when someone merely turns on the light in the room and increases the light level.

Figure 8:
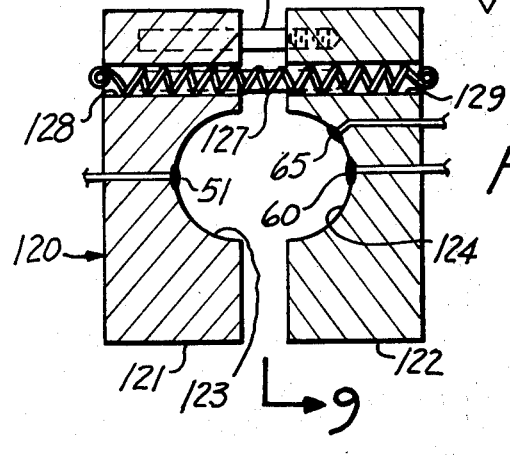
FIG. 8 is a plan view of a mount for use with the invention taken at line 8—8 in FIG. 9.
Figure 11:
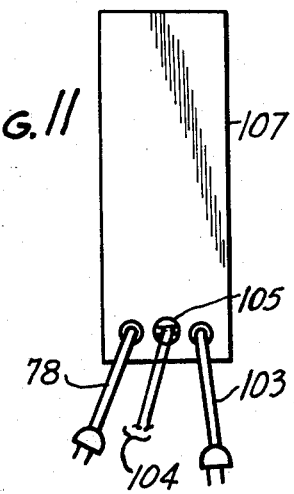
FIG. 11 is a rear view of FIG. 10.

In order to make the device most convenient to use, a clamp 120 (FIG. 8) is provided to hold the sensor means and the two radiation sources against the outside of the wall of the blood chamber. In FIG. 1, the presently preferred form of the blood chamber is schematically shown. It is customarily made of a stiffly flexible, transparent, plastic material which is cylindrical at its midsection and is crimped closed at its top.

Figure 12:
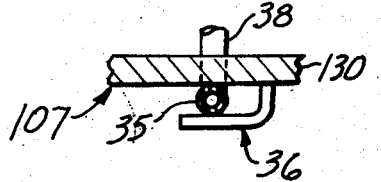
FIG. 12 is a fragmentary cross-section taken at line 12—12 in FIG. 10.
Figure 9:
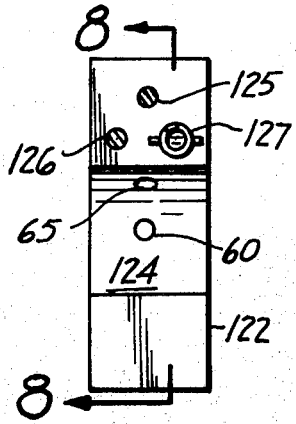
FIG. 9 is a view taken at line 9—9 in FIG. 8.
Figure 10:
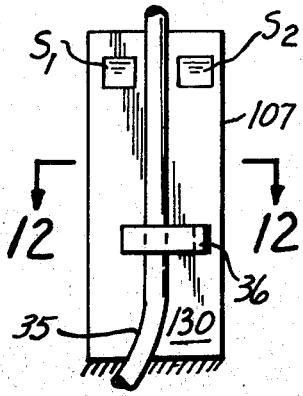
FIG. 10 is a front view of a cabinet useful with this invention.

In normal operation, a closely-controlled amount of air is placed into the blood chamber, so that the flow of blood from the inlet tube can be seen. This assures an observer that blood is actually flowing. The material of the wall is transparent adjacent to the sensor means and radiation sources. The clamp includes a pair of arms 121, 122, each of which has a recessed face 123, 124, respectively. Two alignment rods 125, 126 are threaded into one of the arms and project into a bore in the other so as to prevent relative twisting of the blocks. This arrangement permits them to be moved apart from one another to receive the blood chamber. A tension spring 127 is mounted in bores 128, 129 and connected to the two arms so as to pull them together. The device can be sprung apart to receive the blood chamber and then be sprung back onto the blood chamber to embrace it so that the radiation sources and the sensor means (which are mounted in the recessed faces) are brought against the wall of the blood chamber. At this point, it may be observed that valve 36 can be mounted to the face of cabinet 104 of the device (see FIGS. 10 and 12) with the plunger passing through its front panel 130. This enables the device conveniently to be used by placing the return conduit between the clamp and the face of the cabinet.

The purpose of the sensor means is to exert control over sensitivity adjustment and alarm circuitry 75 (sometimes called a "control"), and thereby over the valve and the pump motor, unless circuitry 75 is disconnected or overridden. The alarm can serve to light up a light 76 or to set off a buzzer 77 or some other annunciator means. Power for circuitry 75 is secured from plug-cord set 103 which can be connected to socket 102 in delivery system 100.

FIG. 4 shows the same blood chamber and first and second radiation sources as FIG. 1. However, the system of FIG. 4 differs from the embodiment of FIG. 1 in that the sensor means comprises a first sensor 85 and a second sensor 86, respectively responsive to the first source and to the second source. This permits additional flexibility in the system design and function. Both sensors will be connected to the sensitivity adjustments and alarm system 75, just as the sensor means was in FIG. 1.

In the use of this device, it is desirable to adjust the sensitivity of the sensor system to the blood of the patient and to prevailing ambient conditions each time the dialysis procedure is started, and to provide means whereby the alarm never fails to sound (if the control is connected and not overridden) when the hematocrit of the blood is less than some safe datum value, for example 10. It is a preferred feature of this invention that a sensitivity adjustment can automatically be provided each time the device is started. Circuitry for this purpose is shown in detail in FIGS. 7, 13 and 14.

The delivery system 100 includes pump 22 and is provided for the handling and protection of the blood delivered to the dialysis mechanism 25. The delivery system itself includes a number of safety monitors, such as for monitoring inlet blood pressure and the like. Many of these monitors include safety cutoff means for stopping the operation of pump 22 in the event of unsatisfactory or dangerous events.

The delivery system 100 receives its power from any suitable source of electricity through a cord-plug set 101. Ultimately, pump 22 will receive its electrical power from this same source, and it may receive it with or without the protection of the sensitivity adjustments and alarm circuitry (control 75), as will now be disclosed.

Socket 102 is "live" unless the safety cutoffs of the delivery system disconnect it. If they do, the pump will be stopped. If the delivery system permits current to socket 102, then control 75 (or its override) will determine whether the pump runs or not. The control cabinet 107 is provided with a socket 105 which receives a cord-plug set 104 from the pump motor 23. Cord sets 103 and 104 are interconnected through a relay switch yet to be described. The control circuitry is effective to control this relay and determine whether the pump can run if there is power at socket 102. The control circuitry could, if desired, be powered from socket 102. However, it is preferable to power the sensor means 50 and control means 75 (sometimes the combination of sensor means 50 and control means 75 are collectively referred to as "detector 106") separately from the current supplied to the pump. Then the control means can be bypassed or disabled, the the pump can still be made to run, which is a convenience in priming and cleaning the system and in checking out malfunctions. Plug-cord 78, which can be connected to any suitable source of electricity, provides for the separate connection of the detector.

Figure 7:
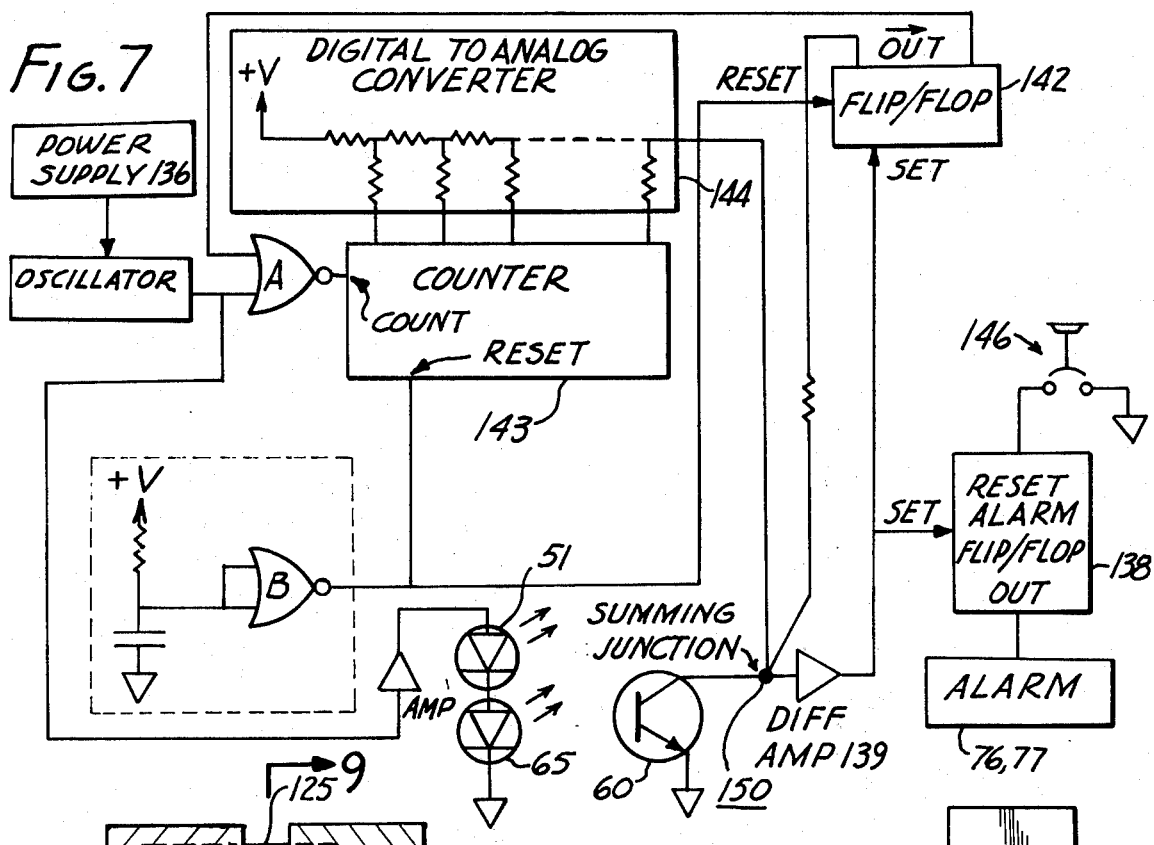
FIG. 7 is a schematic circuit diagram showing circuitry useful with this invention.
Figure 14:
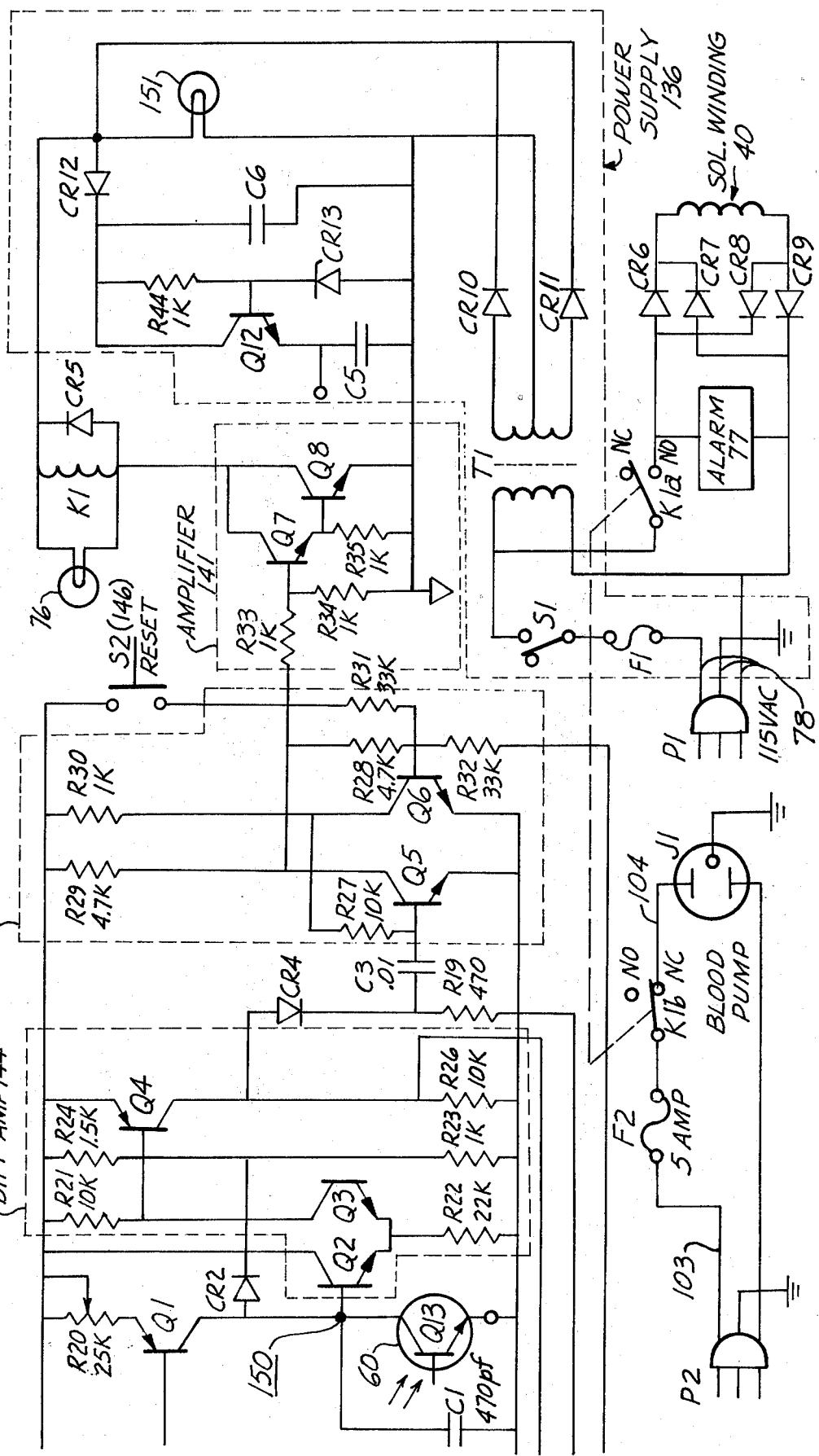
FIGS. 13 and 14 are circuit diagrams showing circuitry suitable for the sensor systems, the left-hand edge of FIG. 14 joining the right-hand edge of FIG. 13.
Figure 13:
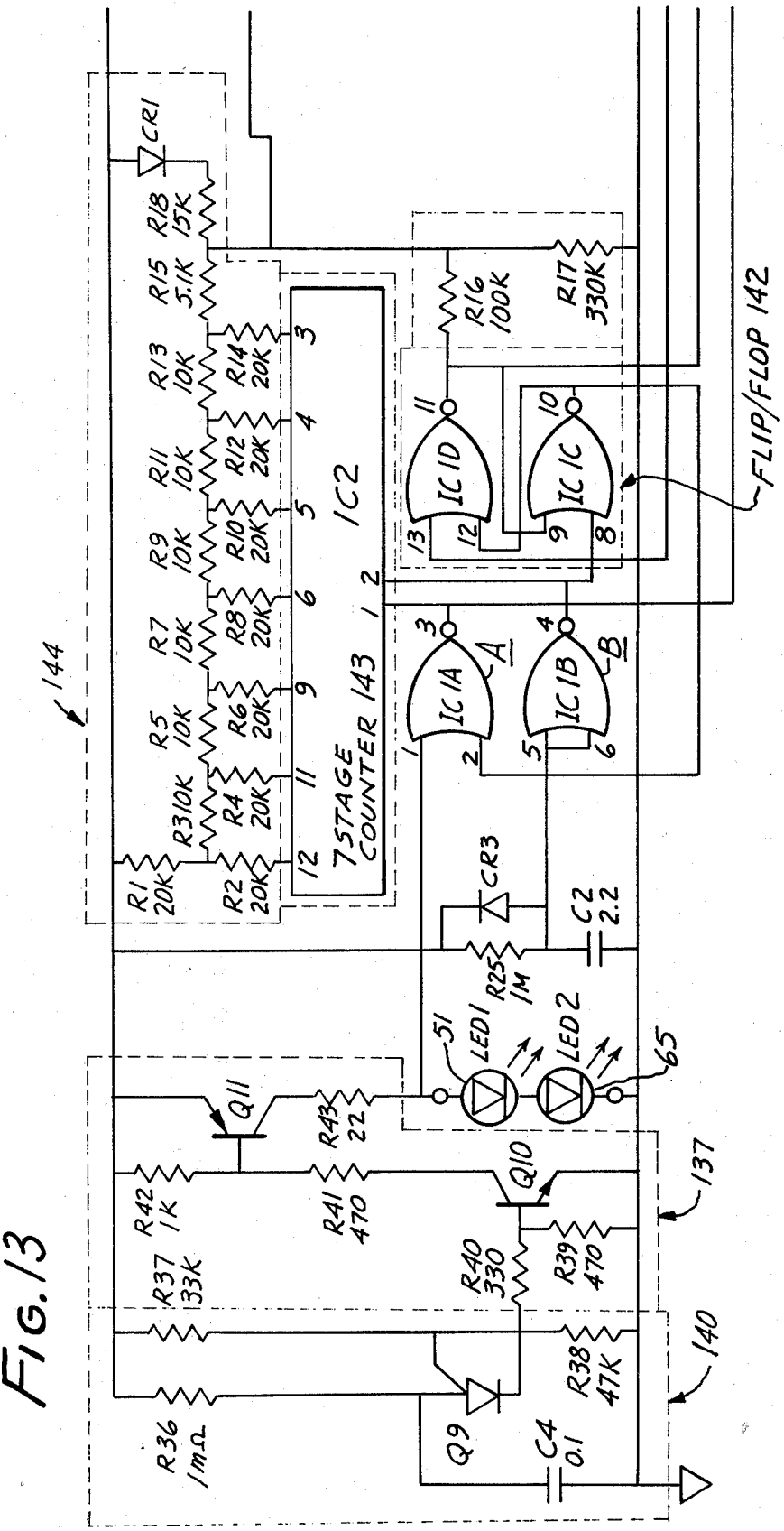

FIG. 7 is a schematic block diagram intended to provide a general understanding of the control, and FIGS. 13 and 14 comprise a circuit diagram of the presently preferred circuitry. Certain of the more important portions of FIGS. 13 and 14 have been shown in FIG. 7. As will ultimately become apparent, the foregoing operation is made possible by a relay K1 (shown only in FIG. 14) which is closed when the control means is disabled, for example, by disconnecting cord 78 or by bypassing it. Then the pump can still operate without interference from the alarm. The control means 75 is therefore optionally useful with the pump.

The detector 106 is shown in further detail in FIGS. 7, 13 and 14. Cord 78 provides current to power supply 136. In turn, the power supply will be connected by means readily apparent to any competent electronic engineer to the various other portions of the invention. An off-on switch S1 is placed ahead of the power supply so as to disable the detector, if desired. This switch may conveniently be installed in the face of cabinet 107. Preferably, it is a two-position, manually operated switch in which each successive actuation turns the power supply on or off. The detector includes a power supply 136, an alarm relay K1, controlling switches K1a and K1b, an amplifier 137, an alarm flip-flop 138, a differential amplifier 139, an oscillator 140, a second amplifier 141, a counter-enable gate A, a power-on reset B, a second flip-flop 142, a seven-stage counter 143, a digital-to-analog converter 144, and an override-reset switch 146 (sometimes shown as "S2"). The radiation sources and sensor are also shown. Particular attention is called to a summing junction 150. (FIGS. 7 and 14)

The components are standard, and their individual identities are as follows:

All resistor values are given in ohms. Capacitor values unless otherwise indicated are in microfarads. The PNP transistors are 2N3644; the NPN transistors are 2N3643.

CR-1 through CR-5 are IN457, CR-6 through CR-9 are IN4004, CR-10 and CR-11 are IN4001. LED1 (radiation source S1) and LED2 are General Electric SSL-55C. Q13 (sensor 60) is General Sensor 4021-2. LED2 may be SSL-55CF (flat lens).

IC1 is CM4001. IC2 is CM4004. Both are obtainable from Radio Corporation of America as Digital Integrated Circuits (monolithic silicon).

Pin 4 of IC's is common. Pin 14 is +12 volts dc.

T1 is a Triad F117X.

Pulsing acutation of the radiation sources increases their radiation output and longevity, compared to steady-current acutation. It is advantageous for the oscillator to produce pulses of a duration of 100 microseconds at a frequency of 10 pulses per second. The resulting radiation will be sensed by sensor means 60 under appropriate circumstances. The lens of source 51 is curved to produce a beam which is either convergent or rather narrowly divergent. The lens of source 61 is flat and produces illumination which is diffuse or divergent. At least it causes radiation over a larger transverse area than the lens of source 51.

The above arrangement will cause the two radiation sources to radiate their infrared radiation as described herein. They are connected in series so that failure of their power, or failure of either one of them to emit their radiation, will cause failure of both.

The precise circuitry shown is not per se part of the invention, but merely shows one means for accomplishing certain of its objectives. Its operation will be clear to any qualified electronic engineer, and no detailed description of its operation appears to be necessary to an understanding of the invention.

Briefly stated, the objectives of the illustrated circuitry are to provide an optional or override operation for the pump, to establish a sensitivity level appropriate to the individual dual dialysis run, and to stop the pump and close the system should air appear in the sensor region.

The function of this system is elegantly simple and straightforward. With all cord sets connected except set 78, or with the circuitry 75 bypassed, then the pump can be operated, even to pump saline solution or very dilute or even aerated blood. Relay K1 is in its repose condition. This same condition would occur even under alarm conditions if switch S2 (switch 146) is closed.

To bring the sensitivity adjustment and alarm circuitry into action, plug 78 is plugged into a suitable source of electrical current, with switch S2 open. Then, assuming that holder 120 is in place, an automatic sensitivity adjustment will take place, and the detector will be in steady-state operation monitoring conditions in the blood chamber, as follows:

Broadly speaking, upon application of power to the detector, the input to power on-reset gate B is held low for approximately 1 to 2 seconds to allow the circuitry to stablize. The oscillator is now running, but the counter is held reset by B. Also, flip-flop 142 is held reset.

After the power-up period has elapsed, the oscillator pulses, which are gated through counter-enable gate A (which is enabled by flip-flop 142), increments the seven-stage counter. The digital to analog converter 144, which is connected to the counter, sinks current increasingly as a function of the increased digital count.

When the current to the summing junction 150 becomes greater than an amount that can be shunted by the sensor 60 (whose conduction is determined by the amount of light incident on its photosensitive element from the sources), the differential amplifier 139 puts out a positive pulse which changes the state of flip-flop 142. Three situations result: (1) an additional current is sunk by a resistor network consisting of R16 and R17, decreasing the sensitivity of the phototransistor circuit; (2) alarm flip-flop 138 is armed so that a sufficient increase of light received by the phototransistor will trigger the alarm; and (3) the counter-enable gate A is disabled so that no further pulses will increment the counter and therefore cannot alter the sensitivity of the device. Should the alarm thereafter be activated, closing the reset switch 146 will reset the alarm flip-flop 138, allowing a further light incursion to sound the alarm, but will not change the automatically preset threshold.

As a consequence of the foregoing, the following results are attained. When the detector is disabled, such as by being disconnected at plug 78 or by opening switch S1, switch K1b is closed, and if the delivery system can provide current, the pump can run. Indicator light 151 would be off, indicating no monitoring function. This can provide the opportunity to run the pump and start the dialysis run.

When monitoring is to start, switch S1 is closed. This starts the above adjustment of sensitivity level, which comprises an automatic stepwise increase in sensitivity (the steps occurring as the counter counts) until an alarm condition is reached, followed by an automatic reduction of sensitivity of about 12%, and then the system locks in. Incidentally, the parameters of the circuit do not permit the sensitivity to ignore a hematocrit below some value, perhaps 10. If radiation reaches the sensor in an amount indicative of air in the blood chamber, conditions at summing junction 150 changes, relay K1 is energized, switch K1b opens to stop the pump, and switch K1a closes to actuate the clamp winding 40 to close the clamp. The system is then shut down, and the alarms are sounded by the annunciator 77 and light 76.

The sounding of the alarm will bring the operator to check what has gone wrong, and if he finds the air or foam condition is minor and can be ignored, he may close override reset switch 146 to resume pumping. But this override operation continues only so long as this switch is held closed. If the operator releases the switch, it opens, and the detector will respond again unless the conditions have improved to the point that the alarm would not have sounded in the first place. The system will not have readjusted itself to a new sensitivity level. This time, if it does not automatically continue when switch 146 is opened, no further effort should be made to start the system, but instead, the problem should be more fully investigated.

It will be noted in FIG. 2 that the radiation sources are connected in series connection. If either fails, or fails to emit its radiation, its failure will shut down the entire system, and its failure will be recognized by the attendant when he makes the first checkout of the system before beginning dialysis. This is to say, before blood is placed in the blood chamber, he should turn on the system and be certain there is an alarm caused by radiation from the first source to the sensor means. If this does not occur, it means that one of the sensor means is not functional.

The detector according to this invention provides a means and a system which, by appropriate shrouding or the use of appropriate radiation, can be completely free from the effects of ambient conditions. It is small, rugged, and can withstand considerable abuse. It is readily checked out, and is foolproof in the sense that it is fail-safe in all of its functions. It is reponsive to the presence of air in the absence of foam or blood, and is responsive to air in the form of foam also, whereby there is no condition wherein a patient, while the sensitivity adjusting and alarm circuitry is connected, can receive air, either as such or included in the blood as foam.

This invention is not to be limited by the embodiments shown in the drawings and described in the description, which are given by way of example and not of limitation, but only in accordance with the scope of the appended claims.

I claim:

1. A sensor system for detecting the absence of substantially air-free blood from a blood chamber, said blood chamber including a wall with a transparent portion, said sensor system comprising: a first radiation source, a second radiation source, each having a respective axis; and sensor means responsive to said radiation, said sensor means being aligned with and intersecting the axis of the first source, and on the other side of the blood chamber therefrom, and being out of alignment with, and not intersecting, the axis of the second source, the radiation from the first source being substantially focused on the sensor means, and the radiation from the second source illuminating a substantial area of said transparent portion lying transverse to its own axis, the sources and sensor means all lying outside of and being directed toward said transparent portion, whereby radiation from the first source is directly perceived by the sensor means when only air lies within the blood chamber between the first source and the sensor means, and not perceived by it when there is blood between the first source and the sensor means, and whereby radiation from the second source is perceived by the sensor means when there is reflection from blood foam in the blood chamber in the path of reflection between the parts of the transparent portion visible to the second source and to the sensor means, and perceived less when there is either foam-free blood, or no blood in the said path of reflection.

2. A sensor system according to claim 1 in which the sensor means has an active condition and a passive condition, one of said conditions being assumed as the consequence of reception of radiation from one of the sources, and in which control means is responsive to the said one condition of the sensor means to terminate the flow of fluid through the blood chamber.

3. A sensor system according to claim 2 in which a pump is driven by a motor to supply fluid to the blood chamber, and in which the control means is adapted and connected to said motor to permit or to prevent its operation to supply fluid.

4. A sensor system according to claim 2 in which a valve is provided at the outlet of the blood chamber selectively to permit or to prevent flow of fluid from the blood chamber, and in which the control means is adapted and connected to determine the flow condition of the valve.

5. A sensor system according to claim 4 in which the valve comprises a clamp adapted to pinch closed a conduit connected to the outlet of the blood chamber to prevent said flow.

6. A sensor system according to claim 2 in which an alarm is provided to notify of the absence of substantially foam-free blood in the blood chamber, and in which the sensor means is adapted and connected to the alarm to activate the alarm in said absence.

7. A sensor system according to claim 2 in which the control means has a sensitivity level, and in which adjustment means is provided to adjust said sensitivity level.

8. A sensor system according to claim 7 in which the said adjustment means initially adjusts to an alarm condition relative to the conditions in the blood chamber, and then automatically decreases the sensitivity to a level which will indicate an alarm condition only upon a deterioration of the condition in the blood chamber by a predetermined increment.

9. A sensor system according to claim 2 in which the control means includes means for setting the sensitivity of the control to a level below that which would activate the control means whereby the control means is activated to terminate the flow of fluid through the blood chamber when the sensor means produces an output responsive to said level.

10. In combination: a sensor system according to claim 9; and an electrical pump motor for pumping the fluid, said motor being powered from a source of power separate from the control means, whereby the motor can be operated when the control means is disabled.

11. A combination according to claim 10 in which an override-reset circuit is provided to disable the control means even when conditions in the blood chamber would activate the same for operating the pump motor independently of the control means.

12. In combination: a sensor system according to claim 2; and an electrical pump motor for pumping the fluid, said motor being powered from a source of power separate from the control means, whereby the motor can be operated when the control means is disabled.

13. A combination according to claim 12 in which an override-reset circuit is provided to disable the control means even when conditions in the blood chamber would activate the same for operating the pump motor independently of the control means.

14. A sensor system according to claim 1 in which said radiation is infra-red radiation.

15. A sensor system according to claim 1 in which the sensor comprises a pair of sensors, and in which each sensor is individually responsive to radiation only from a different and respective one of said sources, radiation from one being perceived directly, and the other by reflection from blood foam.

16. A sensor system according to claim 1 in which the sources are light-emitting diodes.

17. A sensor system according to claim 16 in which said radiation is infra-red radiation.

18. A sensor system according to claim 1 in which said sources are electrically connected in series connection with one another, whereby neither source is actuable in the absence of actual emission of radiation by the other.

19. A sensor system according to claim 1 further including clamp means adapted to clamp onto the outside of the blood chamber, said clamp means including a pair of arms having faces facing toward the blood chamber, the sensor means being carried by said arms and in said faces.

20. A sensor system according to claim 19 in which spring means is provided to hold the clamp means to the blood chamber.

* * * * *